United States Patent [19]
Carlson et al.

[11] Patent Number: 5,800,571
[45] Date of Patent: Sep. 1, 1998

[54] LOCKING MECHANISM FOR VOLUNTARY CLOSING PROSTHETIC PREHENSOR

[75] Inventors: Lawrence Evan Carlson, Boulder, Colo.; Daniel David Frey, Cambridge, Mass.; Eric Stewart Brown, Boulder, Colo.

[73] Assignee: University Technology Corporation, Boulder, Colo.

[21] Appl. No.: 804,545

[22] Filed: Feb. 24, 1997

[51] Int. Cl.[6] ............................................. A61F 2/42
[52] U.S. Cl. ............................ 623/57; 623/63; 56/333
[58] Field of Search ........................... 623/57, 58, 59, 623/63, 64; 56/333

[56] References Cited

U.S. PATENT DOCUMENTS

| | | | |
|---|---|---|---|
| 2,382,404 | 8/1945 | Eberle ............................ | 623/63 |
| 2,557,792 | 6/1951 | Maguth .......................... | 623/57 |
| 3,757,604 | 9/1973 | Schroeder ...................... | 74/529 |
| 4,225,983 | 10/1980 | Radocy et al. . | |
| 4,252,219 | 2/1981 | Kauffman ...................... | 188/69 |
| 4,604,098 | 8/1986 | Seamone et al. ............... | 623/60 |
| 4,865,613 | 9/1989 | Rizzo ............................ | 623/65 |
| 4,886,039 | 12/1989 | Wagner ......................... | 124/23 R |
| 5,062,855 | 11/1991 | Rincoe .......................... | 623/24 |
| 5,367,749 | 11/1994 | Takeuchi ....................... | 24/16 PB |
| 5,401,179 | 3/1995 | Shinchi et al. ................. | 439/157 |

FOREIGN PATENT DOCUMENTS

| | | | |
|---|---|---|---|
| 291784 | 5/1916 | Germany ....................... | 623/57 |
| 309797 | 12/1918 | Germany ....................... | 623/57 |
| 327491 | 10/1920 | Germany ....................... | 623/57 |
| 750013 | 2/1944 | Germany ....................... | 623/57 |
| 116687 | 9/1926 | Switzerland .................... | 623/57 |
| 113923 | 3/1918 | United Kingdom .............. | 623/57 |

*Primary Examiner*—John G. Weiss
*Assistant Examiner*—Bruce E. Snow
*Attorney, Agent, or Firm*—Jennifer L. Bales; Macheledt Bales & Johnson LLP

[57] ABSTRACT

A voluntary closing prosthetic prehensor includes a locking mechanism which may be locked into any position, and released with a small amount of force. With locking enabled, the prehensor opens and closes normally until the user applies sufficient tension to the prehensor cable after the prehensor has closed upon an object. Then, a lever arm attached to the cable rotates, pulling a second cable which causes an elliptical cam to rotate such that its wider portion presses against a pawl, causing the pawl to rotate into engagement with a toothed sector, locking the prehensor closed. When the user releases the force on the cable, the lever arm is biased to return to its normal position, but the prehensor stays closed because the pawl remains engaged with the sector. The cam includes a ratcheting drum which takes up the slack in the second cable. To release the prehensor, the user applies a small amount of force to the first cable, moving the lever arm and pulling the second cable, which rotates the cam. As it starts to rotate, the cam moves away from the pawl, allowing it to rotate away from the sector. The pawl has two links joined at a pivot. The link engaged with the toothed sector pivots to allow the pawl to rotate away from the sector, pulling the engaged link free. The pawl is biased to retract away from the sector, unlocking the prehensor.

12 Claims, 10 Drawing Sheets

LOCKING MECHANISM FOR VOLUNTARY CLOSING PROSTHETIC PREHENSOR

BACKGROUND OF THE INVENTION

1. Field of the Invention

The present invention relates to prosthetic prehensors. More particularly, the present invention relates to locking mechanisms for voluntary closing prosthetic prehensors.

2. Description of the Related Art

Voluntary closing body powered prosthetic prehensors are those which are in an open position unless the user applies cable tension (for example, by bi-scapular abduction, or shoulder shrugging) to close the prehensor. Unless a locking mechanism is provided, the user must maintain constant cable tension in order to hold an object. This requires that the shoulder and involved arm be held stationary, which is tiring and uncomfortable.

It is known in the art to lock voluntary closing prosthetic prehensors by manually inserting the driving cable into a slot using the uninvolved hand. This device has only one locked position (fully closed). In order to disengage the lock, the user displaces the cable from the slot.

A device known as the Army Prosthetics Research Laboratory hand, from Hosmer Dorrance Corporation, allows the voluntary closing prosthetic hand to be locked in any position. Whenever cable tension is applied, the hand closes to a locked position. Subsequent application of cable tension greater than that applied for locking or picking up a heavy object causes the hand to unlock. This device has two disadvantages. First, the hand locks every time it is closed, which is not always what the user desires. Second, it is difficult for the user to unlock the hand if the user locked onto an object with a large amount of force, or the force at the fingertips was increased by picking up a heavy object.

A need remains in the art for a voluntary closing prosthetic prehensor with a locking mechanism which may be locked into any position only when desired, and released with a small amount of force, without requiring the use of the uninvolved hand.

SUMMARY OF THE INVENTION

An object of the present invention is to provide a voluntary closing prosthetic prehensor with a locking mechanism, which may be locked into any position only when desired, and released with a small amount of force, without requiring the use of the uninvolved hand.

The ratchet and pawl locking mechanism of the present invention comprises a sector having a plurality of protruding teeth and a pawl assembly. The pawl assembly includes a link adjacent to the sector having a first end and a second end, wherein the second end of the link pivots with respect to the first end of the link, bringing the second end of the link toward or away from the sector, and a pawl, having a first end and a second end, wherein the first end of the pawl is pivotally connected to the second end of the link, the pawl having a tooth on the second end of the pawl for engaging the sector teeth when the second end of the pawl is brought toward the sector. The mechanism also includes means for selectively locking the mechanism by pivoting the link such that the pawl tooth moves into engagement with the link teeth, and for selectively unlocking the mechanism by pivoting the link such that the second end of the link pivots away from the sector and the pawl pivots with respect to the link until the pawl tooth is pulled free from the sector teeth.

The means for locking the locking mechanism comprises a cam adjacent to the link having a wider portion and a narrower portion and means for rotating the wider portion of the cam into contact with the link to pivot the second end of the link toward the sector. The locking mechanism is unlocked by rotating the wider portion of the cam away from the link to allow the link to pivot the second end of the link away from the sector. The link is biased to to pivot the second end of the link away from the sector.

The cam rotates in only one direction. The means for selectively locking and unlocking includes a cable wound around the cam for rotating the cam when the cable is pulled with sufficient force. A lever arm has a first end attached to the cable and a second end, and a pivot point between the first end and the second end. The lever arm pivots at the pivot point when the second end is moved, thereby pulling the cable.

The locking mechanism further includes a plate forming a base for the cam, the lever arm, and the link. The plate is pivotally attached to the sector. A first stop is attached to the plate adjacent to and on one side of the first end of the lever arm, and a second stop is attached to the plate adjacent to the first end of the lever arm and on the opposite side of the lever arm from the first stop. The lever arm is biased toward the first stop. Thus, force applied to the second end of the lever arm causes the first end of the lever arm to pull the cable, causing the base to pivot with respect to the sector, until a sufficient resistance to the movement of the base is encountered, at which point sufficient force on the first end of the lever arm causes the lever arm to move toward the second stop, applying sufficient force to the cable to rotate the cam.

The finger is rigidly attached to the sector. The thumb is rigidly attached to the plate for moving toward and away from the first finger when the plate rotates. The locking mechanism of claim 8 further includes means for disabling the locking mechanism including means for moving the second stop contiguous to the lever arm when the lever arm is contiguous to the first stop.

DETAILED DESCRIPTION OF THE PREFERRED EMBODIMENT

Figure 1:
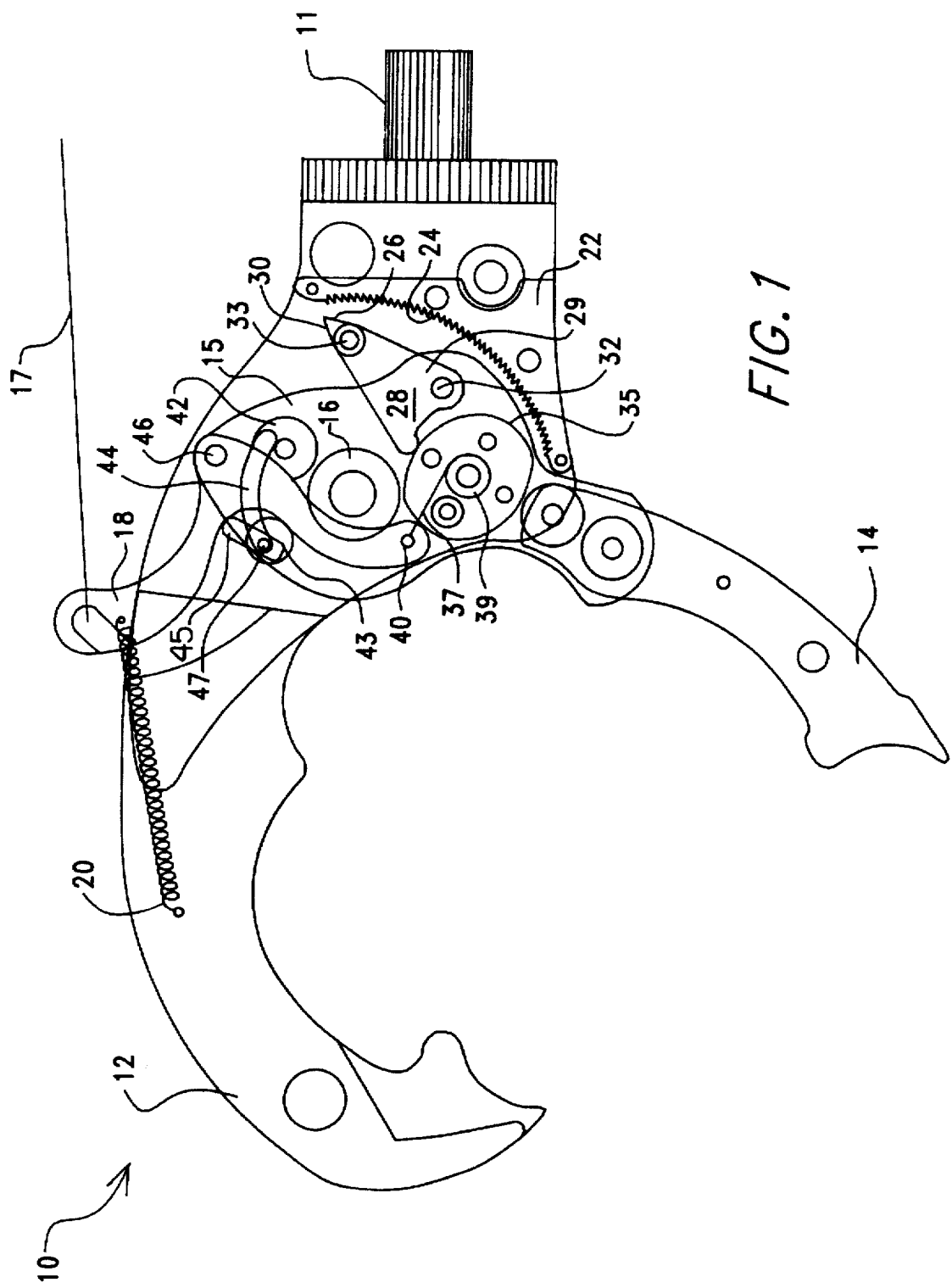
FIG. 1 is a side section view of the preferred embodiment of a locking prehensor according to the present invention, in the open position with the lock disabled.
Figure 2:
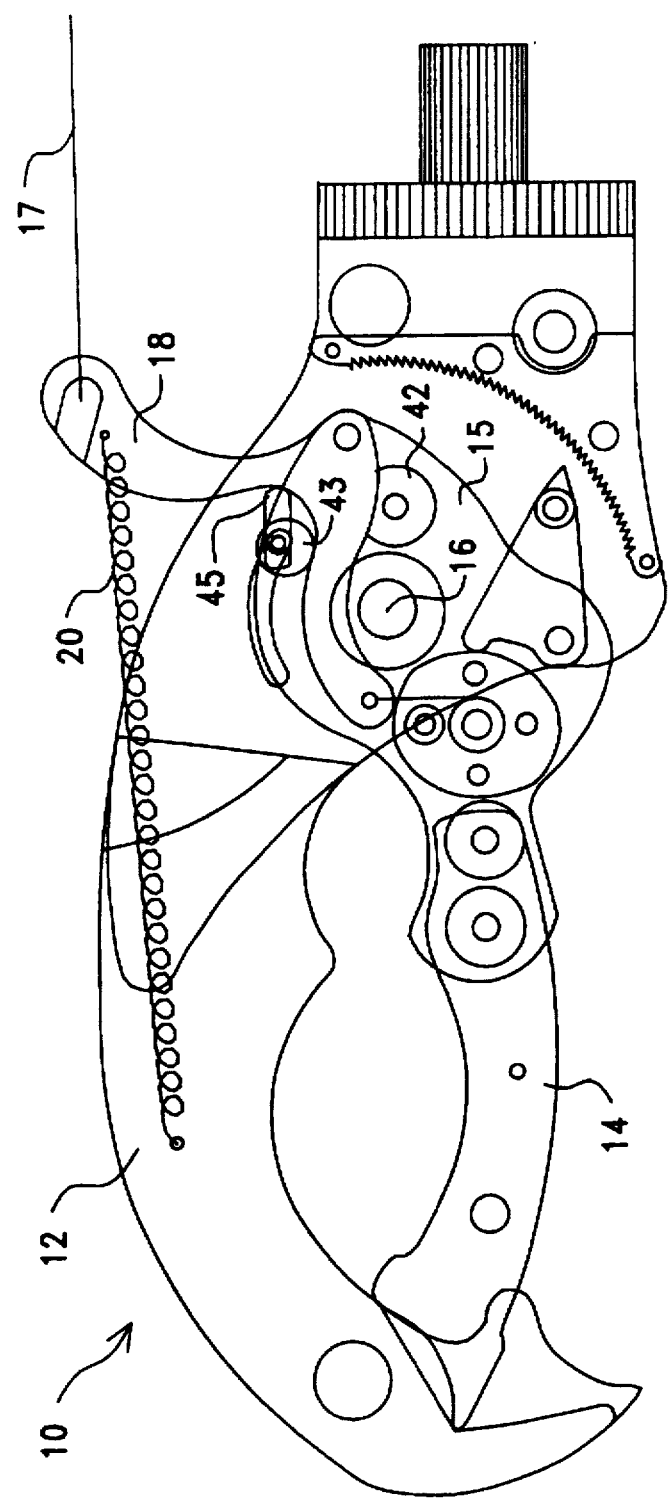
FIG. 2 is a side section view of the locking prehensor of FIG. 1, in the closed position with the lock disabled.

The structure and operation of prehensor 10 will be described in detail in the descriptions associated with FIGS. 1–9 below. FIGS. 1 and 2 show the operation of prehensor 10 with lock 45 disabled, and FIGS. 3–7 show the operation of prehensor 10 with lock 45 enabled. With lock 45 enabled, prehensor 10 opens and closes normally until the user applies sufficient continuing closing force after the prehensor has closed upon an object, or thumb 14 has closed upon finger 12. In other words, if a resistant force of at least a predetermined magnitude is not encountered, the ratcheting lock will not engage, and prehensor 10 will open normally. If the required resistant force is encountered, lever arm 18 rotates clockwise about pivot 46, pulling cable 37, which causes cam 35 to rotate counterclockwise. Cam 35 presses pawl assembly 28, causing it to rotate clockwise into engagement with sector 22, locking prehensor 10 closed. When the user releases the force on cable 17, lever arm 18 returns to stop 42, but prehensor 10 stays closed because tooth 26 of pawl assembly 28 remains engaged with teeth 24 of sector 22. Cam 35 includes over-running clutch or ratcheting drum 39 which takes up the slack in cable 37.

To release prehensor 10, the user applies a small amount of force to cable 17, moving lever arm 18 back against stop 43. This pulls cable 37, rotating cam 35 counterclockwise. As it starts to rotate, cam 35 allows pawl assembly 28 to rotate counterclockwise away from sector 22. Pawl 30 pivots clockwise at pivot 33 with respect to link 29. This motion allows pawl 30 to disengage sector 22, thereby unlocking prehensor 10.

FIG. 1 is a side section view of the preferred embodiment of locking prehensor 10 according to the present invention, in the open position with lock 45 disabled. With lock 45 disabled, prehensor 10 operates like a conventional voluntary closing prosthetic prehensor. Fixed finger 12 is rigidly attached to prosthetic arm connection 11. Thumb 14 is rigidly attached to thumb plate 15, and rotates with respect to finger 12 at main hinge 16. At rest, spring 20 biases lever arm 18 counterclockwise about main hinge 16, causing lever arm 18 to press against stop 42. Stop 44 is rigidly attached to thumb plate 15, so the pressure of lever arm 18 against stop 42 prevents thumb plate 15 and thumb 14 from rotating clockwise toward fixed finger 12.

Lock lever 45 is rigidly connected to stop 43 by pin 47, and protrudes from fixed finger 12 so that a user can access it. Slot 42 in fixed finger 12 allows pin 47 to move with respect to finger 12 when prehensor 10 opens and closes. The user locks and unlocks prehensor 10 by turning lock 45, thereby rotating stop 43.

Thumb 14 is caused to rotate closed as follows. Cable 17 is pulled by the prosthesis wearer, for example, by a shoulder shrug. Lever arm 18 presses against stop 43, which is attached to plate 15. Plate 15 and attached thumb 14 are thus rotated about hinge 16. As thumb 14 closes towards finger 12, prehensor 10 appears as shown in FIG. 2. FIG. 2 is a side section view of locking prehensor 10 of FIG. 1 in the closed position with the lock disabled. Spring 20 is extended between finger 12 and lever arm 18. When the prosthesis wearer releases the tension on cable 17, spring 20 biases lever arm 18 counterclockwise about hinge 16, causing thumb 14 to rotate away from finger 12.

Figure 3:
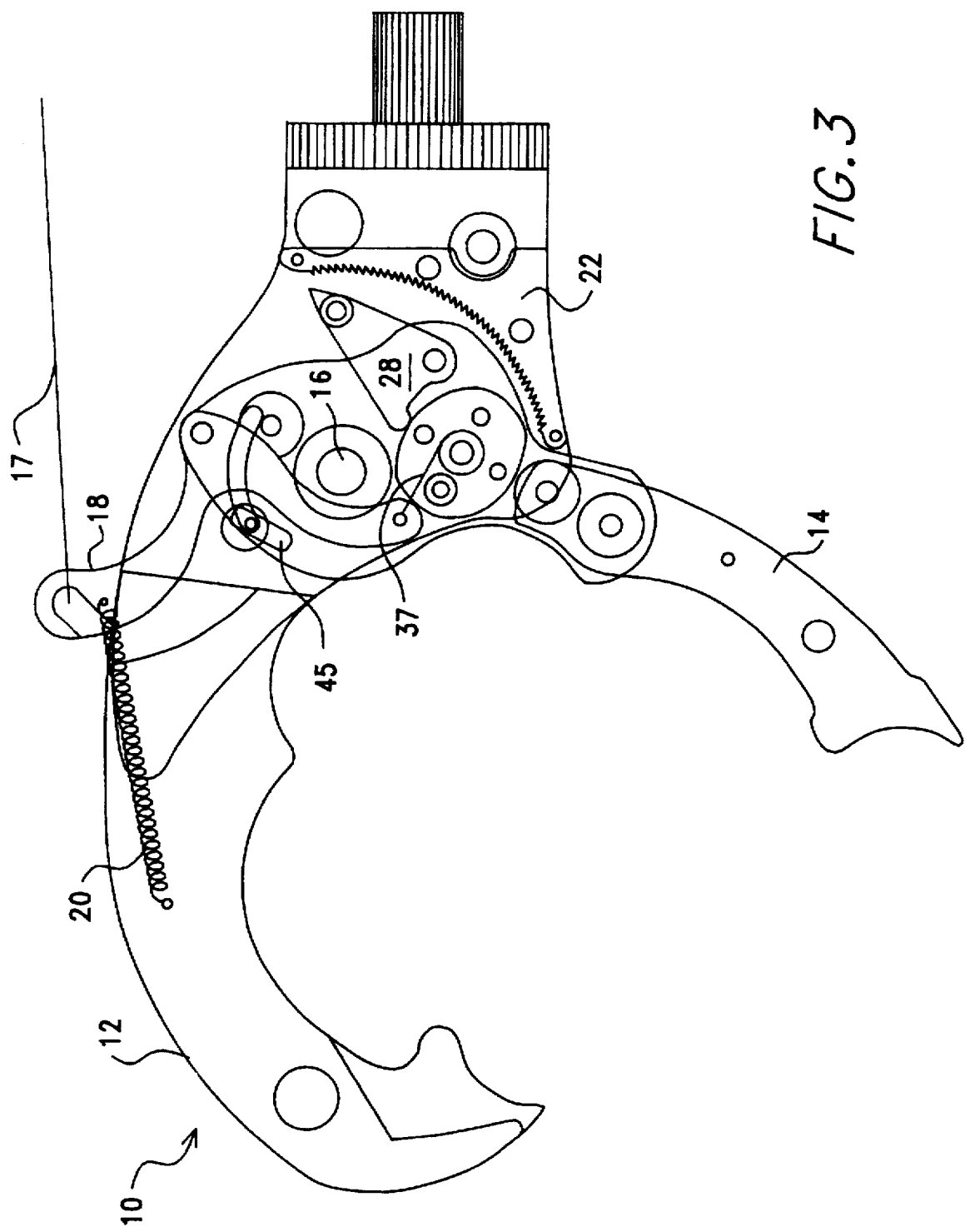
FIG. 3 is a side section view of the locking prehensor of FIG. 1, in the open position with the lock enabled, unlocked, and the lever uncocked.

FIG. 3 is a side section view of the locking prehensor of FIG. 1, in the open position with the lock enabled, unlocked, and the lever uncocked. Stop 43 has been rotated away from lever arm 18 by lock 45, enabling the locking mechanism of the present invention. Now, when cable 17 is pulled, lever arm 18 is able to rotate slightly before it reaches stop 43. As lever arm 18 rotates, it will pull cable 37, as shown in FIG. 5. This will move pawl assembly 28 into contact with sector 22, locking prehensor 10 closed. In FIG. 3, however, lock 45 has simply been enabled. Prehensor must be closed, either as shown in FIG. 4 or against an object, and then further pressure applied as shown in FIG. 5, before prehensor 10 is locked.

Figure 4:
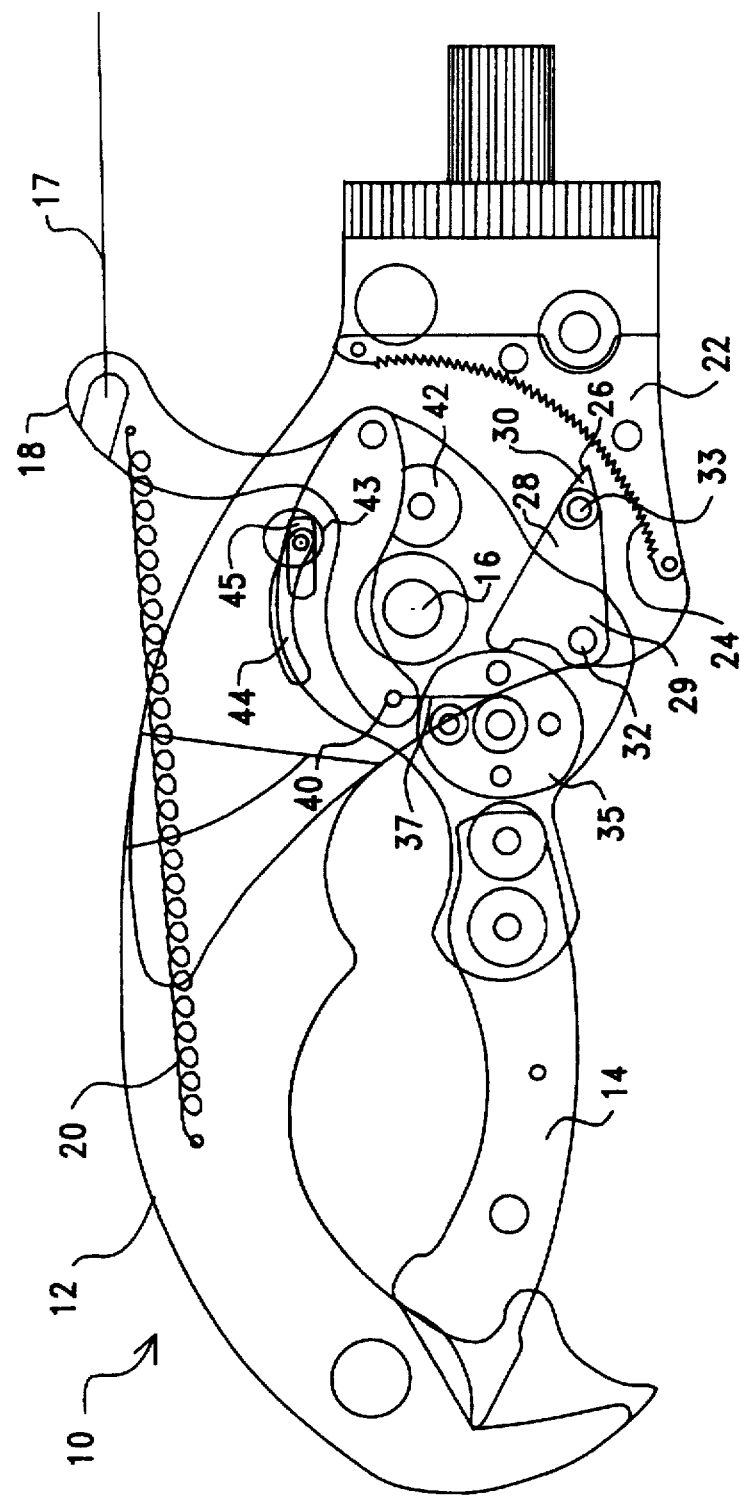
FIG. 4 is a side section view of the locking prehensor of FIG. 1, in the closed position with the lock enabled, unlocked, and the lever uncocked.
Figure 5:
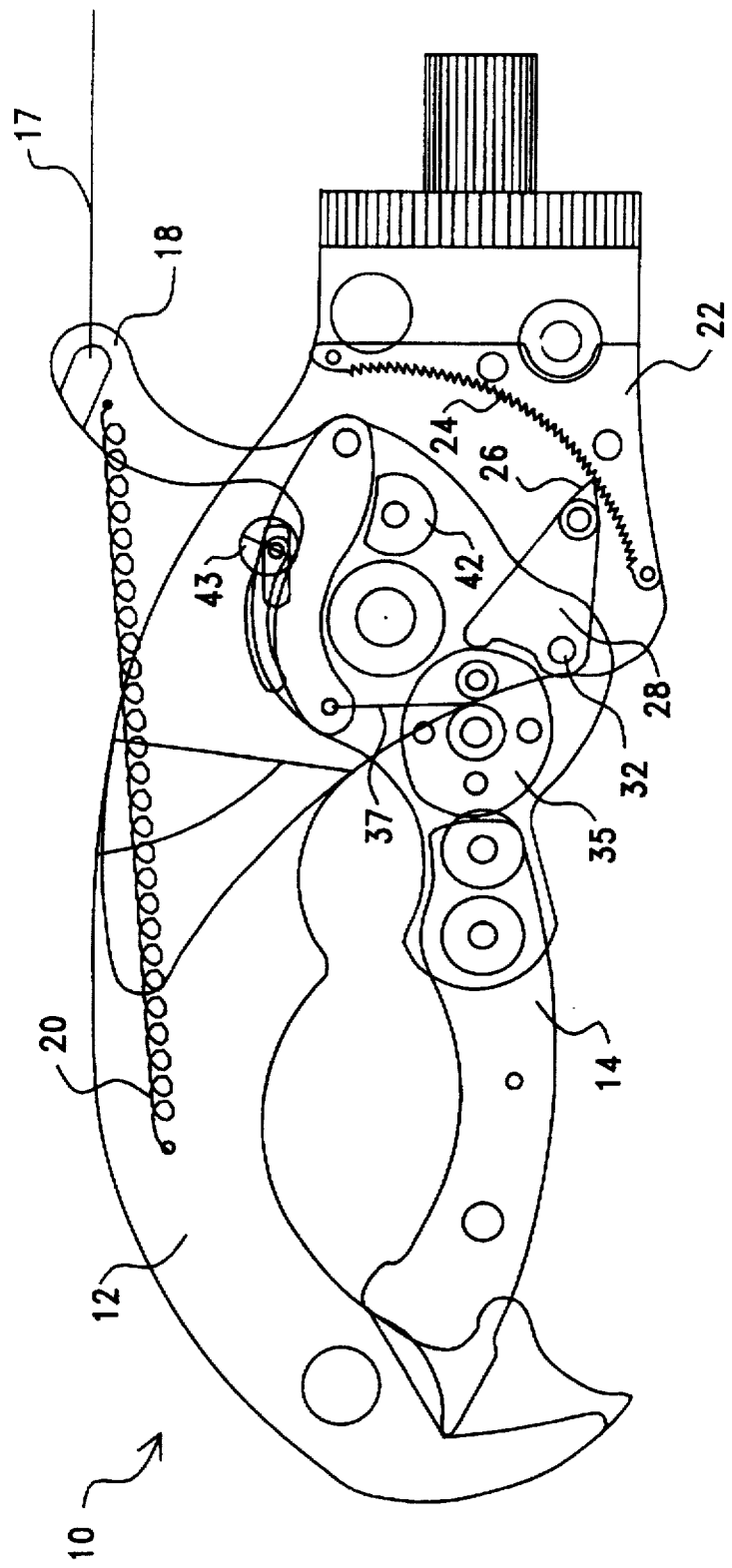
FIG. 5 is a side section view of the locking prehensor of FIG. 1, in the closed position with the lock enabled and locked, and the lever cocked.

FIG. 4 is a side section view of the locking prehensor of FIG. 1, in the closed position with the lock enabled, unlocked, and the lever uncocked. The user has applied enough pressure to cable 17 to close thumb 14, but not enough further pressure has been applied to lock prehensor 10 closed. Thumb 14 closes without lever arm 18 rotating with respect to thumb plate 15 because over-running clutch 39 applies sufficient cable tension to cable 37 to prevent clockwise rotation of lever arm 18.

FIG. 5 is a side section view of the locking prehensor of FIG. 1, in the closed position with the lock enabled and locked, and the lever cocked. In FIG. 5, as in FIG. 4, thumb 14 has closed toward fixed finger 12 until thumb 14 and finger 12 came into contact with each other, and thumb 14 could not rotate anymore. The difference between FIG. 4 and FIG. 5 is that the user continued to pull cable 17 hard enough to overcome the tension in cable 37. Lever arm 18 has rotated clockwise with respect to thumb plate 15, until it hit stop 43. As lever arm 18 rotated clockwise, it pulled cable 37, causing cam 35 to rotate counterclockwise. Cam 35 is non-circular (in this case somewhat elliptical), so that as it rotates counterclockwise, its long portion is brought into contact with pawl assembly 28, causing pawl assembly 28 to rotate clockwise about pivot 32 into contact with sector 22. Prehensor 10 is now locked.

It is important to note that, while in FIG. 5, thumb 14 stops when it hits finger 12, exactly the same sequence would occur if the user had grasped an object between thumb 14 and finger 12. As the user continues to pull on cable 17 after thumb 14 has hit the object, lever arm 18 rotates against stop 43, locking prehensor 10. The only difference between this configuration and that shown in FIG. 5 is that thumb 14 will not be rotated as far counterclockwise, so that tooth 26 of pawl assembly 28 will engage sector teeth 24 further counterclockwise along sector 22.

Figure 6:
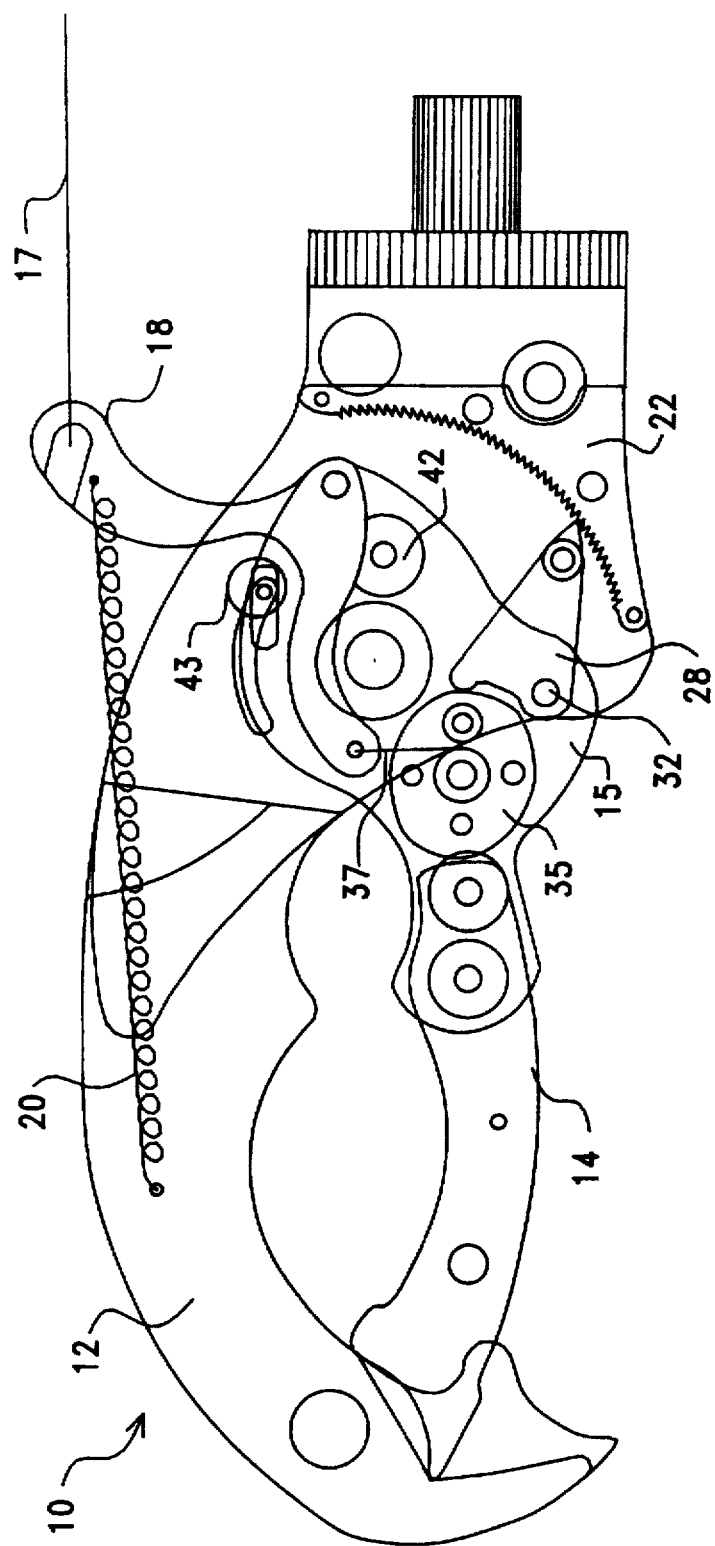
FIG. 6 is a side section view of the locking prehensor of FIG. 1, in the closed position with the lock enabled and locked, and the lever uncocked.

FIG. 6 is a side section view of the locking prehensor of FIG. 1, in the closed position with the lock enabled and locked, and the lever uncocked. The user has released tension on cable 17, allowing lever arm 18 to rotate back against stop 42, but prehensor 10 remains closed because pawl assembly 28 is engaged with sector 22. Thus, the connection point between pawl assembly 28 and thumb plate 15 at pivot 32 is held fixed and thumb plate 15 is likewise held fixed. Cam 35 includes ratcheting drum 39 which takes up the slack in cable 37.

Figure 7:
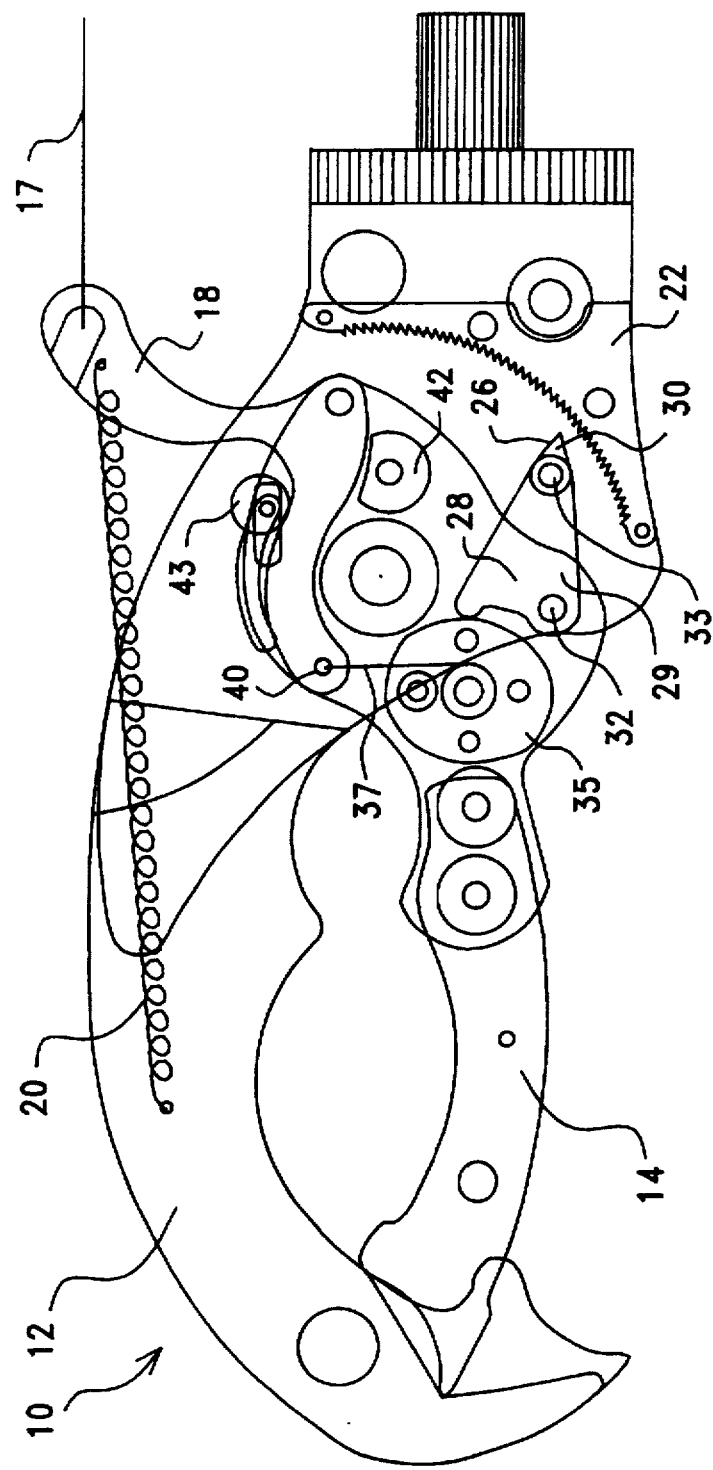
FIG. 7 is a side section view of the locking prehensor of FIG. 1, in the closed position with the lock enabled, lock released, and the lever cocked.

FIG. 7 is a side section view of the locking prehensor of FIG. 1, in the closed position with the lock enabled but unlocked, and the lever cocked. Thus, when the user releases the tension on cable 17, lever arm 18, biased by spring 20, will rotate counterclockwise to stop 42 and press against stop 42, causing thumb plate 15 and thereby thumb 14 to rotate counterclockwise away from finger 12. When prehensor 10 is all the way open, it will have the configuration of FIG. 3.

To release prehensor 10 from its locked configuration, the user applies a small amount of force to cable 17, moving lever arm 18 back against stop 43. Lower end 40 of lever arm 18 pulls cable 37 upward, rotating cam 35 counterclockwise. As it starts to rotate, cam 35 allows pawl assembly 28 to rotate counterclockwise away from sector 22. Pawl 30 pivots clockwise at pivot 33 with respect to link 29. This motion allows pawl 30 to disengage sector 22, thereby unlocking prehensor 10. Pawl assembly 28 is spring biased counterclockwise at pivot 32 to retract away from sector 22. Pawl 30 is also biased at pivot 33 to move back to its normal position, as shown in FIG. 7, after being forced to rotate clockwise in order to pull free of sector 22.

Figure 8:
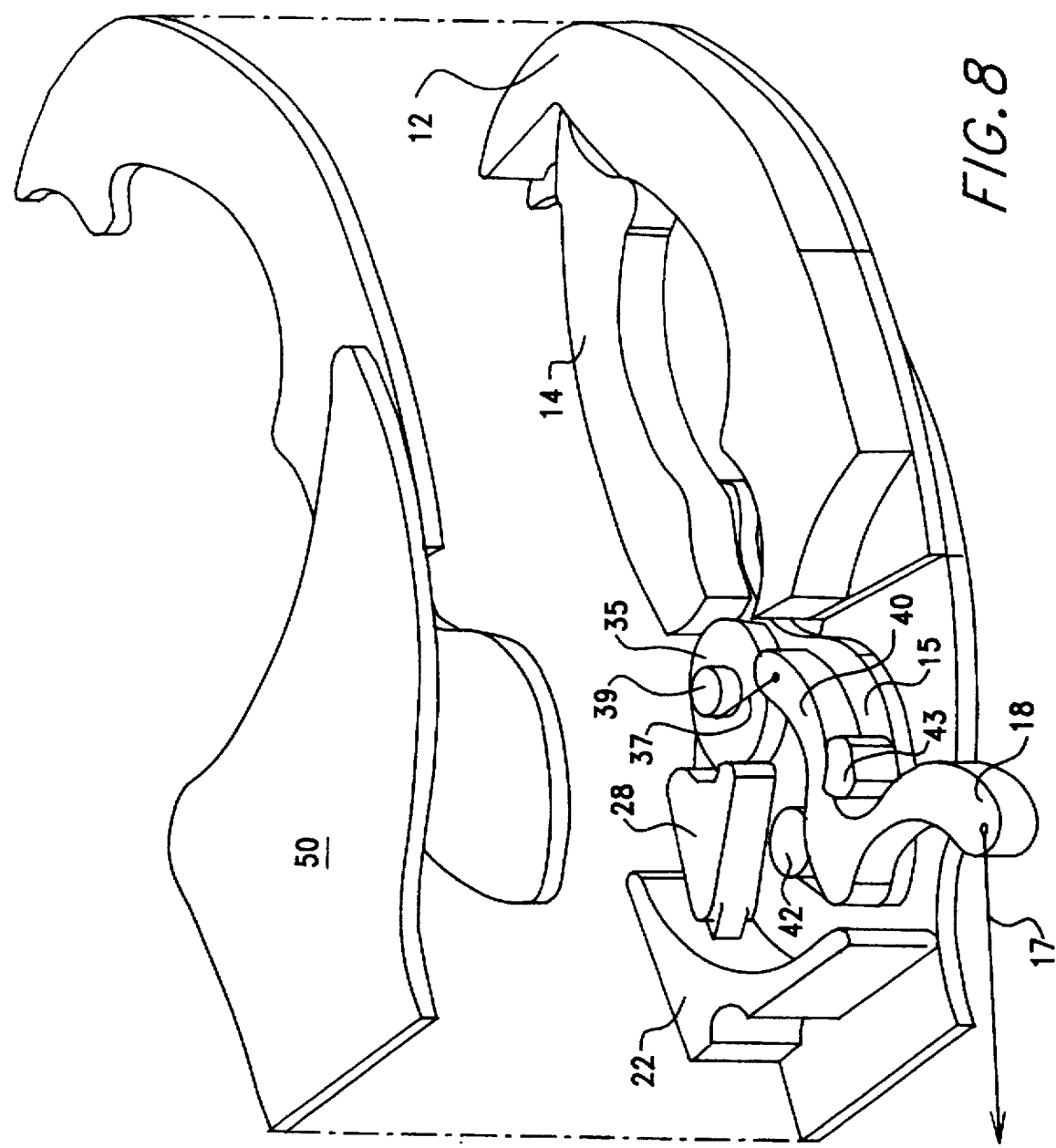
FIG. 8 is an isometric drawing of the locking prehensor of FIG. 1, with the front plate removed.
Figure 9:
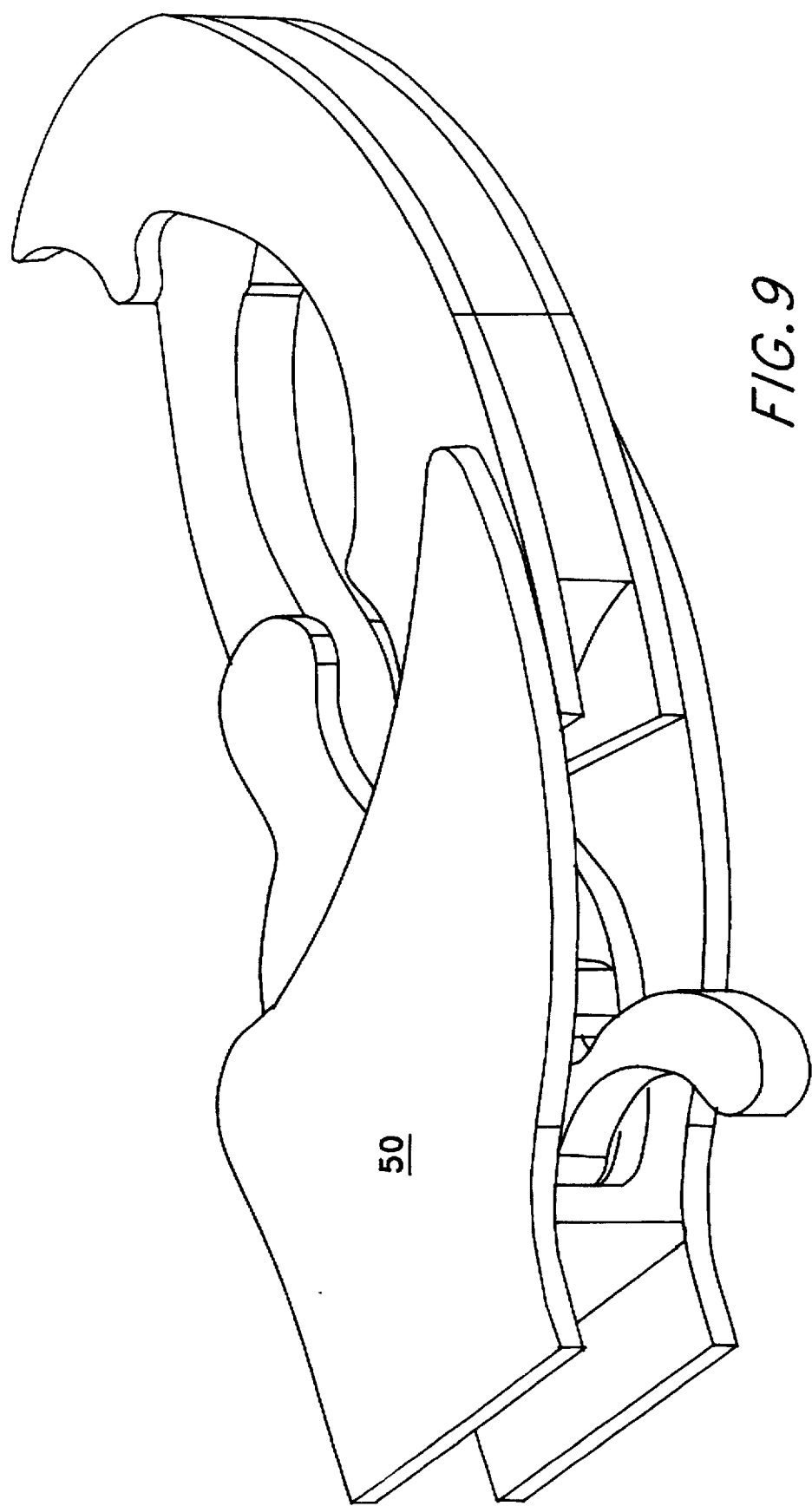
FIG. 9 is an isometric drawing of the locking prehensor of FIG. 1, with the front plate in place.

FIG. 8 is a simplified isometric drawing of locking prehensor 10, with front plate 50 removed. FIG. 8 shows stops 42 and 43 extending upward from thumb plate 15 such that when lever arm 18 presses against stop 42 or 43 it forces thumb plate 15, and thereby thumb 14 to rotate. FIG. 9 is a simplified isometric drawing of locking prehensor 10 with front plate 50 in place.

Figure 10:
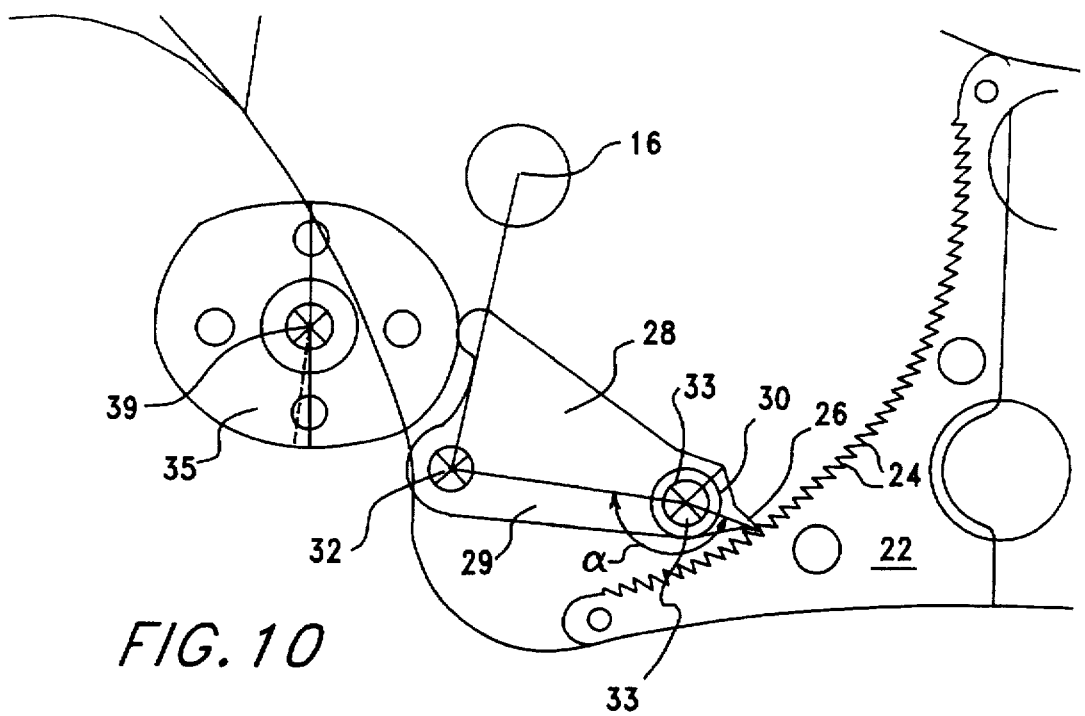
FIG. 10 is a side section detail view of the pawl portion of the locking prehensor of FIG. 1, in the locked position.

FIG. 10 is a side section detail view of pawl assembly 28, cam 35 and sector 22, when prehensor 10 is in a locked position. Other portions of prehensor 10 have been removed for clarity. FIG. 5 shows how prehensor 10 will be configured under these circumstances.

Cam 35 has previously been rotated counterclockwise, and has forced pawl assembly 28 to rotate clockwise into engagement with sector 22. Since cam 35 acts as an over-running clutch, in this case via ratcheting drum 39, cam 35 will continue to hold pawl assembly 28 in the engaged position until it is again rotated counterclockwise. The wearer of prehensor 10 can close thumb 14 further. In that case, pawl 30 is dragged down and to the left, and tooth 26 eventually catches on a lower tooth 24 of sector 22.

Thumb 14 may not open with respect to finger 12, however, because an attempt to open prehensor 10 forces tooth 26 directly into sector 22. Lines connecting pivot point 16 (pivot point of thumb 14), pivot point 32 (pivot point of pawl assembly 28) and tooth 26 form a 90 degree angle, as is standard in ratchet and pawl designs. In the locked position, lines connecting pivot 32, pivot 33 (pivot point of pawl 30) and tooth 26 form an angle slightly less than 180-degrees (angle alpha in FIG. 10). Opening force at the fingers tends to rotate pawl 30 with respect to link 29, buckling pawl assembly 28 upward, but cam 35 prevents this from happening by preventing link assembly 28 from rotating counterclockwise. Stops on link 29 and pawl 30 of pawl assembly 28 prevent angle alpha from quite reaching (or exceeding) 180-degrees.

Figure 11:
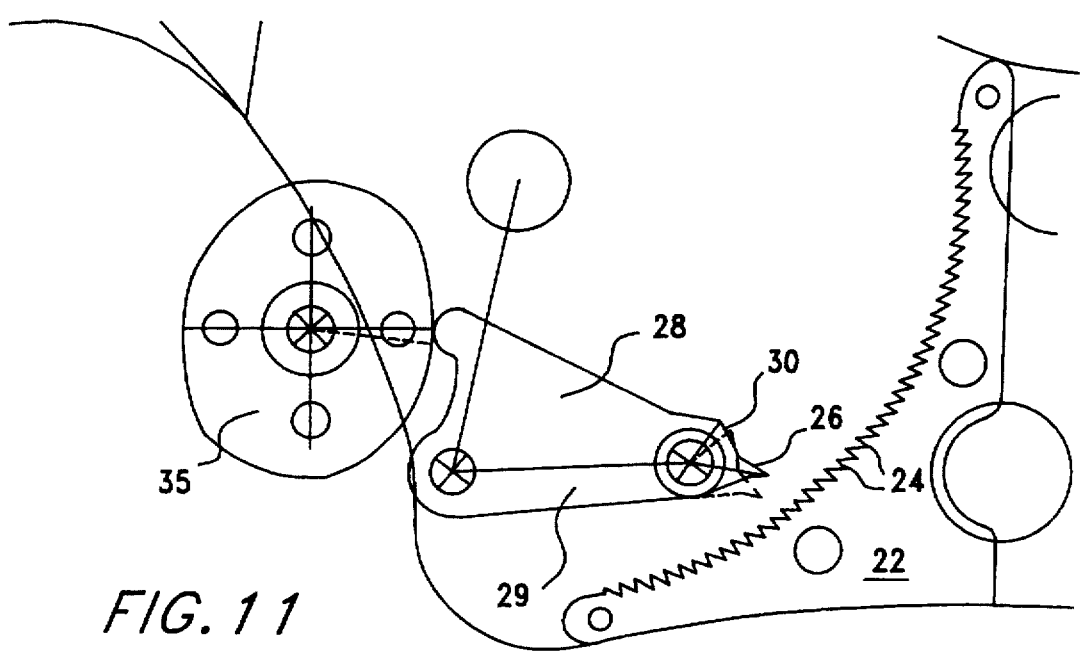
FIG. 11 is a side section detail view of the pawl portion of the locking prehensor of FIG. 1, in the unlocked position.

FIG. 11 is a side section detail view of pawl assembly 28, cam 35 and sector 22, when prehensor 10 is in an unlocked position. Other portions of prehensor 10 have been removed for clarity. FIG. 7, among others, shows how prehensor 10 will be configured under these circumstances.

When cam 35 is again rotated counterclockwise (as described above), its smaller radius portion is disposed toward pawl assembly 28. Since pawl assembly 28 is biased (e.g., spring loaded) towards the unlocked position, it springs back to that position. Pawl 30 is forced to rotate clockwise about pivot 33 as link 29 rotates counterclockwise about pivot 32, because it is caught by tooth 24 of sector 22. In other words, pawl assembly 28 buckles upward. Once link 29 has rotated far enough, tooth 26 is pulled free of tooth 24 of sector 22. At this point, pawl 30 springs back into its normal position with respect to pawl assembly 28, as it, too, is spring loaded.

What is claimed is:

1. A ratchet and pawl locking mechanism comprising:

a ratchet including a sector having a plurality of protruding teeth;

a pawl assembly, base means attached to the pawl assembly for locating the pawl assembly adjacent to the ratchet;

said pawl assembly including:

a link pivotally attached to the base means, said link having a first end and a second end, wherein the second end of the link pivots with respect to the first end of the link thereby bringing the second end of the link toward or away from the sector, and a pawl, having a first end and a second end, wherein the first end of the pawl is pivotally connected to the second end of the link, said pawl having a tooth on the second end of the pawl for engaging the sector teeth when the second end of the pawl is brought toward the sector; and means for selectively locking and unlocking the mechanism by pivoting the link such that the pawl tooth moves into and out of engagement with the sector teeth including:

a cam adjacent to the link having a wider portion and a narrower portion, said cam rotationally attached to the second finger and capable of rotating in only one direction;

a cable wound around the cam for rotating the cam when the cable is pulled with sufficient force, whereby to lock the mechanism the wider portion of the cam is rotated into contact with the link to pivot the second end of the link toward the sector, such that the pawl tooth moves into engagement with the sector teeth, and to unlock the mechanism the wider portion of the cam is rotated away from the link to allow the link to pivot the second end of the link away from the sector, whereby the pawl pivots with respect to the link until the pawl tooth is pulled free from the sector teeth; and means for biasing the link to pivot the second end of the link away from the sector to unlock the mechanism.

2. The locking mechanism of claim 1, further including:

a lever arm having a first end attached to the cable and a second end; the lever arm pivotally attached to the base means at a pivot point between the first end and the second end, the lever arm pivoting at the pivot point when the second end is moved, thereby pulling the cable.

3. The locking mechanism of claim 2, wherein said base means is pivotally attached to the sector and further including:

a first stop attached to said base means adjacent to and on one side of the first end of the lever arm;

a second stop attached to said base means adjacent to the first end of the lever arm and on the opposite side of the lever arm from the first stop; and means for biasing the lever arm toward the first stop;

whereby force applied to the second end of the lever arm causes the first end of the lever arm to pull the cable, causing the base means to pivot with respect to the sector, until a sufficient resistance to the movement of the base means is encountered, at which point sufficient force on the first end of the lever arm causes the lever arm to move toward the second stop, applying sufficient force to the cable to rotate the cam.

4. The locking mechanism of claim 3, further comprising:

a first finger rigidly attached to the sector; and a second finger rigidly attached to the base means for moving toward and away from the first finger when the base means rotates.

5. The locking mechanism of claim 4, further comprising:

means for disabling the locking mechanism including means for moving the second stop contiguous to the lever arm when the lever arm is contiguous to the first stop.

6. A voluntary closing prosthetic prehenser comprising:

a first finger;

a second finger pivotally attached to the first finger; and a ratchet and pawl locking mechanism for selectively fixing the first finger in relation to the second finger, said locking mechanism including:

a ratchet including a sector having a plurality of protruding teeth rigidly attached to the first finger;

a pawl assembly pivotally attached to the second finger, said pawl assembly including:

a link having a first end and a second end, wherein the second end of the link pivots with respect to the first end of the link, bringing the second end of the link toward or away from the sector, and a pawl, having a first end and a second end, wherein the first end of the pawl is pivotally connected to the second end of the link, said pawl having a tooth on the second end of the pawl for engaging the sector teeth when the second end of the pawl is brought toward the sector; and means for selectively locking and unlocking the mechanism by pivoting the link such that the pawl tooth moves into and out of engagement with the sector teeth including:

a cam adjacent to the link having a wider portion and a narrower portion, said cam rotationally attached to the second finger and capable of rotating in only one direction;

a cable wound around the cam for rotating the cam when the cable is pulled with sufficient force, whereby to lock the mechanism the wider portion of the cam is rotated into contact with the link to pivot the second end of the link toward the sector, such that the pawl tooth moves into engagement with the sector teeth, and to unlock the mechanism the wider portion of the cam is rotated away from the link to allow the link to pivot the second end of the link away from the sector, whereby the pawl pivots with respect to the link until the pawl tooth is pulled free from the sector teeth; and means for biasing the link to pivot the second end of the link away from the sector to unlock the mechanism.

7. The prehenser of claim 6, further including:

a lever arm having a first end attached to the cable and a second end; the lever arm having a pivot point between the first end and the second end, the lever arm pivoting at the pivot point when the second end is moved, thereby pulling the cable.

8. The prehenser of claim 7, further including:

a plate forming a base for the cam, the lever arm, and the link, said plate rigidly attached to the second finger;

a first stop attached to said plate adjacent to and on one side of the first end of the lever arm;

a second stop attached to said plate adjacent to the first end of the lever arm and on the opposite side of the lever arm from the first stop; and means for biasing the lever arm toward the first stop;

whereby force applied to the second end of the lever arm causes the first end of the lever arm to pull the cable, causing the base to pivot with respect to the sector, until a sufficient resistance to the movement of the base is encountered, at which point, sufficient force on the first end of the lever arm causes the lever arm to move toward the second stop, applying sufficient force to the cable to rotate the cam.

9. The prehenser of claim 8, further comprising:

means for disabling the locking mechanism including means for moving the second stop contiguous to the lever arm when the lever arm is contiguous to the first stop.

10. A voluntary closing prosthetic prehensor comprising:

a finger;

a thumb pivotally attached to the finger; and a locking mechanism for selectively preventing the thumb from pivoting away from the finger when the mechanism is locked, said locking mechanism including:

a sector having a plurality of protruding teeth rigidly attached to the finger;

a pawl assembly pivotally attached to the thumb, said pawl assembly including:

a link adjacent to the sector having a first end and a second end, wherein the second end of the link pivots with respect to the first end of the link, bringing the second end of the link toward or away from the sector, and a pawl, having a first end and a second end, wherein the first end of the pawl is pivotally connected to the second end of the link, said pawl having a tooth on the second end of the pawl for engaging the sector teeth when the second end of the pawl is brought toward the sector; and means for selectively locking and unlocking the mechanism by pivoting the link such that the pawl tooth moves into and out of engagement with the sector teeth, said means for selectively locking and unlocking comprising a cam adjacent to the link having a wider portion and a narrower portion, and a cable wound around the cam for rotating the wider portion of the cam either into contact with the link to pivot the second end of the link toward the sector, or away from the link to allow the link to pivot the second end of the link away from the sector, and means for biasing the link to pivot the second end of the link away from the sector.

11. The prehenser of claim 10, wherein said cam rotates in only one direction, and wherein the means for selectively locking and unlocking further comprises:

a lever arm having a first end attached to the cable and a second end; the lever arm having a pivot point between the first end and the second end, the lever arm pivoting at the pivot point when the second end is moved, thereby pulling the cable.

12. The prehenser of claim 11, further comprising:

a plate forming a base for the cam, the lever arm, and the link, said plate rigidly attached to the thumb;

a first stop attached to said plate adjacent to and on one side of the first end of the lever arm;

a second stop attached to said plate adjacent to the first end of the lever arm and on the opposite side of the lever arm from the first stop; and means for biasing the lever arm toward the first stop;

wherein force applied to the second end of the lever arm causes the first end of the lever arm to pull the cable, thereby causing the base to pivot with respect to the sector, until a sufficient resistance to the movement of the base is encountered, at which point sufficient force on the first end of the lever arm causes the lever arm to move toward the second stop, applying sufficient force to the cable to rotate the cam.

* * * * *